United States Patent
Megonnell

(12) 
(10) Patent No.: US 6,949,219 B1
(45) Date of Patent: Sep. 27, 2005

(54) METHOD FOR DISINFECTION OF ACTIVATED CARBON THROUGH CONTACT WITH PEROXIDE CONTAINING MATERIALS

(75) Inventor: Neal Megonnell, Coraopolis, PA (US)

(73) Assignee: Calgon Carbon Corporation, Pittsburgh, PA (US)

(*) Notice: Subject to any disclaimer, the term of this patent is extended or adjusted under 35 U.S.C. 154(b) by 0 days.

(21) Appl. No.: 10/319,322

(22) Filed: Dec. 13, 2002

(51) Int. Cl.$^7$ .............................. A61L 9/00; A61L 2/00; B01J 19/00
(52) U.S. Cl. .................. 422/34; 422/1; 422/5; 422/28; 422/32; 422/40; 422/292
(58) Field of Search .................. 422/1, 5, 28, 32, 422/34, 40, 292

(56) References Cited

U.S. PATENT DOCUMENTS 4,121,039 A * 10/1978 Parthasarathy et al.
4,812,173 A * 3/1989 Tsao et al. .................. 134/27
5,135,714 A * 8/1992 Wang
5,723,717 A * 3/1998 Kiss
6,261,457 B1 * 7/2001 Wenthold et al. ........... 210/636

FOREIGN PATENT DOCUMENTS

GB  2 248 559 A  *  6/1991  .......... B01D 41/04
JP  362136289 A  *  6/1987  ............. C02F 1/28

OTHER PUBLICATIONS

Disinfection, Sterilization, and Preservation, Seymour S. Block, fourth edition, pp. 621-622; 179-180; 859.*

* cited by examiner

Primary Examiner—Robert J. Warden, Sr.
Assistant Examiner—Monzer R. Chorbaji
(74) Attorney, Agent, or Firm—Christine W. Trebilcock; Cohen & Grigsby, P.C.

(57) ABSTRACT

A process is provided for the disinfection of activated carbon. The process comprises contacting contaminated carbon with peroxide-containing materials for a sufficient amount of time using enough peroxide to provide effective disinfection in a process that is relatively non-hazardous, convenient, and carbon-friendly.

24 Claims, No Drawings

METHOD FOR DISINFECTION OF ACTIVATED CARBON THROUGH CONTACT WITH PEROXIDE CONTAINING MATERIALS

FIELD OF THE INVENTION

The present invention relates the use of peroxide-containing materials for disinfection of activated carbon contaminated with microorganisms.

BACKGROUND OF THE INVENTION

Activated carbon has been utilized to purify water, air, and various chemicals through the process of adsorption; however, activated carbon has also been well established as a source of bacteriological contamination. Naturally occurring bacteria inherent to material being purified (water, air, etc.) will inhabit the pore structure of the activated carbon. The result is the periodic need to disinfect the activated carbon to prevent unacceptable levels of these bacteria from exiting the activated carbon in the purified solution. This issue is very prevalent in the water purification industry for applications such as potable water purification. Various processes have been utilized over the years in an attempt to disinfect the activated carbon, however, each process has drawbacks that make the process unattractive.

Standard disinfectants such as chlorine have been utilized for many years in an attempt to disinfect activated carbon. Chlorine however will react chemically with the activated carbon structure, over time weakening the carbon skeleton and therefore physically degrading the activated carbon. The reaction of chlorine with activated carbon is also kinetically very rapid; therefore, the entire bed of activated carbon is not disinfected. The use of high levels of chlorine will also cause the generation of trihalomethanes, which are known carcinogens.

Various caustic solutions and acids have also been utilized over the years to disinfect activated carbon, with varying degrees of success. The process relies on a significant change in the pH of the solution to disinfect the activated carbon. Because of using high or low pH solutions, large volumes of acidic or basic waste is generated, which must be neutralized for safe disposal. Materials of construction must also be taken into account since the low or high pH can be corrosive to various metals or concrete. The disposal and materials of construction issues prevent disinfection by caustic solution or acid from being technically or economically feasible.

Other disinfection methods such as steaming are routinely utilized in industries such as brewing and bottling. The process involves the introduction of steam to a bed of activated carbon, holding the carbon bed at temperature for several hours, cooling, and rinsing prior to reestablishing flow to the carbon unit. This process although technically feasible, is not practical for various industries such as large municipal drinking water systems.

All of the prior art methods for disinfection of activated carbon have certain disadvantages, which make the processes unattractive from either a technical or economical basis. Chief among them is the generation of various waste products, which require disposal or create corrosion issues.

Accordingly, it is the object of the present invention to provide an improved process for the disinfection of activated carbon using peroxide-containing materials. It is a further the object of this invention to provide a disinfection process that does not generate harmful by-products, generate waste products requiring disposal, or cause materials of construction issues.

SUMMARY OF THE INVENTION

In general, the present invention is directed towards a process for the disinfection of an activated carbon contaminated with microorganisms comprising contacting the activated carbon with a peroxide-containing material. Contacting is conducted by a dynamic or static process for a sufficient amount of time and using enough residual peroxide in the water to allow the peroxide to penetrate through the entire carbon bed. In the present method the use of peroxides possessing the —O—O— chemical functionality has been found to provide an effective disinfectant in that the peroxide reacts sufficiently slowly with the carbon allowing for disinfection throughout the entire carbon bed. The peroxides are degraded by the activated carbon to relatively innocuous or adsorbable by-products such as oxygen and water in the case of hydrogen peroxide, or sodium carbonate/bicarbonate and oxygen in the case of sodium percarbonate.

The process utilizes any activated carbon including, for example, carbon derived from a carbon-containing material. Activated carbon can be a fiber, fabric, cloth or the like; formed bonded or otherwise incorporated into a unitized body for use as filtration media; granular, pelleted, shaped or powder.

The peroxide-containing material comprises a peroxide possessing the peroxyl (—O—O—) chemical functionality. Preferably, the peroxide-containing material is compatible with drinking water sytems and is hydrogen peroxide, a persalt, a peracid or any combination thereof. The peroxide-containing material can be part of an aqueous or non-aqueous solution and stabilized or non-stabilized against autodecomposition. In one embodiment, the peroxide-containing material is generated in situ through a chemical reaction.

The peroxide-containing material is present in an amount sufficient in the water to get through the entire carbon bed. In an embodiment, the peroxide-containing material concentration in solution is less than 250 mg/L or, preferably, less than 1,000 mg/L. The concentration of the peroxide-containing material can be produced from higher concentration peroxide solutions, including those up to 50% solutions. The peroxide ranges selected are to be high enough to insure the entire carbon bed receives a reasonable level of peroxide and likely vary with carbon catalytic activity towards peroxide destruction as well as the available time to disinfect. In another embodiment utilizing a catalytically active carbon, peroxide-containing material is minimally 200 ppm.

In a preferred embodiment of the present method, the peroxide-containing material is hydrogen peroxide in a range of about 5 ppm to 10,000 ppm. The contacting of the peroxide-containing material is undertaken for 5 minutes for dynamic disinfection and to 24 hours for static disinfection. As an example, with the use of a 10 foot diameter vessel operating at a maximum of around 1200 grams per minute (gpm), the activated carbon bed residing within the vessel would have contact with the peroxide-containing material for 5 minutes. However, when static disinfection is used with the 10 foot diameter vessel operating at a maximum of around 1200 gpm the peroxide solution is pumped through the vessel until the peroxide is detected in the effluent and then let sit for 24 hours subsequent to that. In a dynamic disinfection scenario, the peroxide-containing material is pumped through the vessel at contact times of at least 5 minutes, wherein the peroxide-containing material is pumped through the vessel for a minimum of 15 minutes and a maximum of 24 hours.

Other features, aspects and advantages of the present invention will become better understood or apparent from a perusal of the following preferred embodiments and appended claims.

PRESENTLY PREFERRED EMBODIMENTS

The utility of the invention is illustrated by the following two examples. Example 1 demonstrates the disinfection process uses a dynamic process where the peroxide solution is continuously passed through the bed of activated carbon. Example 2 demonstrates the disinfection process using a static process where the peroxide solution is introduced and held in the bed of activated carbon, and discharged after a period of time.

EXAMPLE 1

A ten-foot diameter carbon adsorption unit filled with 20,000 lbs of activated carbon was installed for treatment of drinking water. Prior to allowing the treated drinking water to be distributed to the public for consumption, the treated water was analyzed for total coliform bacteria. Analysis of the water showed a positive result for total coliform bacteria, thus preventing the treated water from being distributed for public consumption. The carbon bed was disinfected by introducing a 240 mg/L solution of hydrogen peroxide upwards through the carbon unit at a flowrate of 800 gallons per minute for two hours and 55 minutes. A sample of treated water was collected several days later and analyzed for total coliform bacteria. Data show the treated water was negative for total coliform bacteria, thus allowing distribution of the treated drinking water.

EXAMPLE 2

A ten-foot diameter carbon adsorption unit filled with 20,000 lbs of activated carbon was installed for treatment of drinking water. Prior to allowing the treated drinking water to be distributed to the public for consumption, the treated water was analyzed for total coliform bacteria. Analysis of the water showed 2–4 CFU/.1 L for total coliform bacteria, thus preventing the treated water from being distributed for public consumption. A 200 mg/L solution of hydrogen peroxide was introduced upwards through the carbon unit at 200–400 gallons per minute until hydrogen peroxide was detected in the outlet of the carbon adsorption unit. The peroxide solution remained in contact with the carbon bed for twelve hours, was discharged, and was rinsed with clean, bacteria-free water for ten minutes. A sample of treated water was collected three days later and showed non-detectable concentrations of total coliform bacteria. Samples of treated water collected three and four months later showed non-detectable levels of total coliform bacteria.

While the foregoing has been set forth in considerable detail, the embodiments and preferences are presented for elucidation and not limitation. It will be appreciated from the specification that various modifications of the invention and combinations of elements, variations, equivalents, or improvements therein may be made by those skilled in the art, and are still within the scope of the invention as defined in the appended claims.

What is claimed is:

1. A process for the disinfection of an activated carbon comprising contacting an activated carbon contaminated with microorganisms with a water compatible peroxide-containing material, wherein said peroxide-containing material is peroxide or possesses peroxyl (O—O—) chemical functionality.

2. A process as set forth in claim 1, wherein said peroxide-containing material comprises one of the group consisting of hydrogen peroxide, persalt, peracid and any combination thereof and wherein said peroxide-containing material is part of a non-aqueous solution.

3. A process as set forth in claim 1, wherein said peroxide-containing material is part of an aqueous solution or a non-aqueous solution.

4. A process as set forth in claim 3, wherein the concentration of said peroxide-containing material in solution is less than 250 mg/L.

5. A process as set forth in claim 3, wherein the concentration of said peroxide-containing material in solution is less than 1000 mg/L.

6. A process as set forth in claim 3, wherein the concentration of said peroxide-containing material in solution is produced from higher concentration peroxide solutions.

7. A process as set forth in claim 3, wherein said peroxide-containing material in solution is produced from at least one higher concentration peroxide-containing solution, wherein said higher concentration is at most 50% in peroxide.

8. A process as set forth in claim 3, wherein said peroxide-containing material is hydrogen peroxide, and wherein the hydrogen peroxide is in a range of about 5 to about 10,000 ppm.

9. A process as set forth in claim 3, wherein said peroxide-containing material is hydrogen peroxide, and wherein the hydrogen peroxide contacts said activated carbon in a static disinfection process for 24 hours.

10. A process as set forth in claim 3, wherein said peroxide-containing material is hydrogen peroxide, and wherein the hydrogen peroxide contacts said activated carbon in a dynamic disinfection process for at least 5 minutes.

11. A process as set forth in claim 1, wherein said peroxide-containing material is generated in situ through a chemical reaction.

12. A process as set forth in claim 11, wherein the concentration of said peroxide-containing material in solution is less than 250 mg/L.

13. A process as set forth in claim 11, wherein the concentration of said peroxide-containing material in solution is less than 1000 mg/L.

14. A process as set forth in claim 11, wherein the concentration of said peroxide-containing material in solution is produced from higher concentration peroxide solutions.

15. A process as set forth in claim 11, wherein said peroxide-containing material in solution is produced from at least one higher concentration peroxide-containing solution, wherein said higher concentration is at most 50% in peroxide.

16. A process as set forth in claim 11, wherein said peroxide-containing material is hydrogen peroxide, and wherein the hydrogen peroxide is in a range of about 5 to about 10,000 ppm.

17. A process as set forth in claim 11, wherein said peroxide-containing material is hydrogen peroxide, and wherein the hydrogen peroxide contacts said activated carbon in a static disinfection process for 24 hours.

18. A process as set forth in claim 11, wherein said peroxide-containing material is hydrogen peroxide, and wherein the hydrogen peroxide contacts said activated carbon in a dynamic disinfection process for at least 5 minutes.

19. A process as set forth in claim 1, wherein said process for disinfection is dynamic or static.

20. A process as set forth in claim 1, wherein said activated carbon is granular, pelleted, shaped or powdered.

21. A process as set forth in claim 1, wherein said activated carbon is formed, bonded or otherwise incorporated into a unitized body for use as a filtration media.

22. A process as set forth in claim 1, wherein said activated carbon is a fiber, fabric or cloth.

23. A process as set forth in claim 1, wherein said activated carbon is derived from any carbon-containing material.

24. A process as set forth in claim 1, wherein said peroxide-containing material is stabilized or non-stabilized against autodecomposition.

* * * * *